United States Patent
Heintz et al.

(10) Patent No.: US 11,266,827 B2
(45) Date of Patent: Mar. 8, 2022

(54) MIXED IONIC ELECTRONIC CONDUCTORS FOR IMPROVED CHARGE TRANSPORT IN ELECTROTHERAPEUTIC DEVICES

(71) Applicant: Battelle Memorial Institute, Columbus, OH (US)

(72) Inventors: Amy M. Heintz, Dublin, OH (US); Krenar Shqau, Columbus, OH (US); Ramanathan Lalgudi, Westerville, OH (US); Katherine M Palmer, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 140 days.

(21) Appl. No.: 16/080,303

(22) PCT Filed: Apr. 10, 2018

(86) PCT No.: PCT/US2018/026981
§ 371 (c)(1),
(2) Date: Aug. 27, 2018

(87) PCT Pub. No.: WO2018/191317
PCT Pub. Date: Oct. 18, 2018

(65) Prior Publication Data
US 2020/0238073 A1 Jul. 30, 2020

Related U.S. Application Data
(60) Provisional application No. 62/483,942, filed on Apr. 10, 2017.

(51) Int. Cl.
*A61N 1/04* (2006.01)
*C08J 5/02* (2006.01)
*H01B 1/24* (2006.01)

(52) U.S. Cl.
CPC .............. *A61N 1/0496* (2013.01); *C08J 5/02* (2013.01); *A61N 1/0436* (2013.01);
(Continued)

(58) Field of Classification Search
CPC .. A61N 1/0496; A61N 1/0436; A61N 1/0452; A61N 1/0456; C08J 5/02; C08J 2309/04; H01B 1/24
See application file for complete search history.

(56) References Cited

U.S. PATENT DOCUMENTS 5,376,107 A 12/1994 Inagi et al.
6,718,212 B2 4/2004 Parry et al.
(Continued)

FOREIGN PATENT DOCUMENTS

DE 102008010876 B4 10/2012
EP 0057877 B1 10/1985

OTHER PUBLICATIONS

Kaur, Gagan, et al. "Electrically conductive polymers and composites for biomedical applications." Rsc Advances 5.47 (2015): 37553-37567. (Year: 2015).*

(Continued)

*Primary Examiner* — Gary Jackson
*Assistant Examiner* — Alexander M Eisenberg
(74) *Attorney, Agent, or Firm* — Susanne A. Wilson; Frank Rosenberg

(57) ABSTRACT

This invention addresses the need for efficient dry skin electrodes. Robust, flexible Mixed Ionic Electronic Conductor (MIEC) electrodes were prepared by an aqueous solution route resulting in electrically conductive networks of carbon nanotubes (CNTs) and ionically conductive elastic matrix. The flexible electrode was characterized in terms of conductivity, ionic charge transfer resistance, and water uptake.

(Continued)

The flexible electrode maintained low resistance even after multiple cycles of 50% extension and contraction.

15 Claims, 6 Drawing Sheets

(52) U.S. Cl.
CPC .......... *A61N 1/0452* (2013.01); *A61N 1/0456* (2013.01); *C08J 2309/04* (2013.01); *H01B 1/24* (2013.01)

(56) References Cited

U.S. PATENT DOCUMENTS

| | | | |
|---|---|---|---|
| 8,862,223 | B2 | 10/2014 | Yanaki |
| 9,248,278 | B2 | 2/2016 | Crosby et al. |
| 9,253,878 | B2 | 2/2016 | Kobayashi et al. |
| 9,675,358 | B2 | 6/2017 | Wagner et al. |
| 10,010,272 | B2 | 7/2018 | Wisniewski et al. |
| 10,279,170 | B2 | 5/2019 | Syed et al. |
| 2007/0093789 | A1 | 4/2007 | Smith |
| 2009/0068244 | A1* | 3/2009 | Weber .................. A61L 27/443 424/423 |
| 2010/0023101 | A1* | 1/2010 | Wallace .................. D01F 1/09 514/1.1 |
| 2010/0068461 | A1* | 3/2010 | Wallace .............. B81C 1/00111 428/156 |
| 2010/0114273 | A1 | 5/2010 | Muccio |
| 2010/0173228 | A1 | 7/2010 | Wallace et al. |
| 2011/0021965 | A1* | 1/2011 | Karp ...................... A61L 15/64 602/54 |
| 2011/0024158 | A1* | 2/2011 | Tsotsis ..................... H01B 1/24 174/126.1 |
| 2011/0210282 | A1* | 9/2011 | Foley ..................... B82Y 25/00 252/62.51 R |
| 2012/0058889 | A1* | 3/2012 | Nishino ................ C01B 32/174 502/328 |
| 2014/0090884 | A1 | 4/2014 | Kobayashi et al. |
| 2014/0276247 | A1* | 9/2014 | Hall ........................ A61P 35/00 601/2 |
| 2016/0104554 | A1* | 4/2016 | Zhong ..................... H01B 1/24 264/425 |
| 2016/0155530 | A1* | 6/2016 | Someya ................ A61B 5/686 174/257 |
| 2016/0303361 | A1* | 10/2016 | Sameti ................... A61K 31/55 |
| 2017/0273590 | A1 | 9/2017 | Maesani et al. |
| 2019/0137436 | A1 | 5/2019 | Lillehoj et al. |

OTHER PUBLICATIONS

International Preliminary Report on Patentability for PCT Application No. PCT/US2018/026981, dated Oct. 15, 2019.
International Search Report and Written Opinion for PCT Application No. PCT/US2018/026981, dated Jun. 11, 2018.
Aregueta-Robles, et al., "Organic electrode coatings for next-generation neural interfaces", Frontiers in Neuroengineering, 2014, vol. 7, pp. 1-18, Graduate School of Biomedical Engineering, University of New South Wales, Sydney, NSW, Australia.
Moulton et al., "Liquid Crystal Behavior of Single-Walled Carbon Nanotubes Dispersed in Biological Hyaluronic Acid Solutions", JACS, 2007, vol. 129, No. 30, pp. 9452-9457.
Extended European Search Report for EP Application No. EP20162880.7, dated Jul. 22, 2020.
Machine translation of DE Patent No. DE102008010876B4.

\* cited by examiner

MIXED IONIC ELECTRONIC CONDUCTORS FOR IMPROVED CHARGE TRANSPORT IN ELECTROTHERAPEUTIC DEVICES

RELATED APPLICATIONS

This application is a national stage filing and claims the priority benefit of PCT/US18/26981 filed 10 Apr. 2018 and also claims priority to U.S. Provisional Patent Application No. 62/483,942, filed 10 Apr. 2017. The disclosures of these applications are incorporated by reference.

INTRODUCTION

The goal that led to the invention was to develop a conductive, elastomeric electrode for use in electrotherapeutic medicine. The electrode can be used in neuromuscular electrical stimulation (NMES) and iontophoretic drug delivery.

Conventional electrodes for electrotherapeutic devices use a metal or inorganic conductive material (e.g., TiN, Ir—$IrO_2$, Pt) plus a coupling layer (e.g., electrolyte). An electrode is placed where a redox reaction takes place between the device and the tissue of patient. Thus, it must conduct both electrons and ions. The reactions can be faradaic or capacitive, involving the charging and discharging of the electrode-electrolyte double layer. Capacitive charge injection is more desirable than faradaic charge injection because no chemical species are created or consumed during a stimulation pulse. Most conventional electrodes are faradaic or pseudo-capacitive, which can lead to performance changes over time. In addition, under the high rate of charge injection and high current density conditions of a neuromuscular stimulation pulse, access to all the accessible charges is limited by the interfacial resistance and low surface area at the electrode. For durable electrodes, a low resistance that does not vary with time or humidity is required.

The current state of organic electrode coatings has been reviewed by Aregueta-Robles et al. in "Organic electrode coatings for next-generation neural interfaces," Frontiers in Neuroengineering, vol. 7, pp. 1-18 (May 2014). The authors reported that blending hydrogels with conductive components such as CNTs may provide desired electrical characteristics with reduced stiffness. Wallace et al. in US Published Patent Application No. 2010/0173228 discuss nanostructured composites which may contain CNTs and biomolecules such as hyaluronic acid.

The present invention provides novel electrode materials that will advance electrotherapeutic medicine.

SUMMARY OF THE INVENTION

An important aspect of this invention is that the electrical and ionic conductors are embedded in the matrix in such a way that the electrical and ionic elements achieve percolation, i.e., a continuous interconnected network, at lower loading than would be achieved by simple random mixing. This allows the electrical performance to be achieved while retaining the necessary mechanical properties.

In a first aspect, the invention provides an electrode, comprising:
coalesced elastomer particles, CNTs, and a glycosaminoglycan; wherein the CNTs and glycosaminoglycan are disposed on the exterior of the coalesced elastomer particles. This solid structure may be observed by optical or electron microscopy and well-known techniques for analyzing composition such as Auger spectroscopy. The coalescence of latex particles occurs naturally as the suspension medium is removed. The individual components may be additionally identified by well-known techniques from the dispersed or partially dissolved electrode such as chromatography and spectroscopy.

In a second aspect, the invention provides an electrode, comprising:
elastomer, CNTs, and a glycosaminoglycan; and characterizable by: a conductivity of at least 1000 mS/cm that changes by less than 10% after 5 strain cycles of extending the material by 50% and allowing the material to contract. While the first aspect of the invention is based on chemical knowledge; the second aspect is directly tied to superior and surprising observed results; and thus the second aspect is a necessary and important alternative way to define the invention. In some preferred embodiments, the invention can be characterized as possessing both the first and second aspects.

In another aspect, the invention provides a method of making a flexible electrode suitable for neuromuscular electrical stimulation, comprising: forming an aqueous dispersion of CNTs and a glycosaminoglycan; combining the aqueous dispersion with an aqueous emulsion of an elastomer to form a composite precursor; and depositing the precursor onto a surface, removing water, and curing the elastomer to form the electrode. The method may further comprise treating the electrode with aqueous sodium chloride.

In another aspect, the invention provides an electrode, comprising: coalesced polymeric particles, electrical conductor, and ionic conductor; wherein the electrical conductor and ionic conductor are disposed on the exterior of the coalesced polymeric particles. In some preferred embodiments, the polymeric particles are elastomeric.

In a further aspect, the invention provides an electrode, comprising: coalesced polymeric particles comprising ionically conductive moieties that are bonded to the coalesced polymeric particles, and electrical conductor; wherein the electrical conductor and ionic conductor are disposed on the exterior of the coalesced polymeric particles. Preferably, the ionically conductive moieties are covalently bonded to the coalesced polymeric particles.

The electrode of any of the above aspects may be configured in the shape of a cuff or disposed in an apparatus (such as a sleeve) comprising an array of the electrodes.

In a further aspect, the invention provides a method of administering a medicine through the skin, comprising: applying any of the electrodes described herein onto the skin of an animal; wherein the electrode comprises a medicine; and applying a potential across the electrode.

In another aspect, the invention provides a method of conducting neuromuscular electrical stimulation (NMES), comprising: applying the electrode of any of the previous claims onto the skin of an animal; and generating a current through the electrode to activate a muscle.

In some preferred embodiments, the invention can be further characterized by any one or any combination of the following: the electrode comprising 0.1 to 2 wt % CNTs, preferably 0.2 to 1 wt %, in some embodiments 0.5 to 0.8 wt % CNTs; the electrode comprising 0.1 to 5 wt % glycosaminoglycan, preferably 0.4 to 4 wt %, in some embodiments 0.7 to 3 wt % glycosaminoglycan; the electrode comprising 10 to 60 wt % water, preferably 20 to 50 wt %, in some embodiments 30 to 50 wt % water; the electrode comprising a mass ratio of glycosaminoglycan to CNT in the range of 0.5 to 5, preferably 1 to 3, and in some embodiments 1.5 to 2.5; the electrode comprising at least 0.01 wt % Na, or 0.01 to 2 wt % Na, in some embodiments 0.1 to 1 wt % Na; wherein the electrode has a thickness and two major surfaces; and wherein at least 30 wt % of the CNTs are disposed on a major surface or within the 10% of the thickness near a major surface; wherein the electrode possesses a conductivity of 1000 mS/cm to about 3000 mS/cm that changes by less than 10% after 5 strain cycles of extending the material by 50% and allowing the material to contract; wherein the electrode possesses a ratio of partial conductivity of a charge carrier to the total conductivity, transference number, $t_i$ of at least 0.10, preferably at least 0.13, in some embodiments in the range of 0.10 to about 0.20 or 0.15 to about 0.20.

In some preferred embodiments the electrode comprises one or more of the following: wherein the electrode has a top and bottom surface, wherein the bottom surface is adapted to contact the skin of a patient, wherein the electrode has a graded structure with an increasing ratio of ionic conductor to electrical conductor from the top to the bottom of the electrode; wherein the gradient is prepared by layer-by-layer fabrication of the electrode, with increasing levels of ionic conductor in successive layers; preferably having at least 3 layers or at least 5 layers; wherein the elastomeric particles comprise nitrile butadiene rubber, natural rubber, silicone, Kraton-type, silicone acrylic, polyvinylidene fluoride, polyvinylidene chloride, or polyurethane, or combinations thereof; wherein, in the emulsion prior to curing, at least 90 mass % of the polymer particles are in the size range of 50 nm to 10 µm in diameter; wherein the electrical conductors have a number average aspect ratio of height to the smallest width dimension of at least 10; wherein the electrical conductor comprises carbon nanotubes, graphene, graphite structures, and metal nanowires, and combinations thereof; wherein the ionic conductor comprises hyaluronic acid, fluorosulfonic acids like Nafion™, sulfated polysaccharides and other mucoadhesive type compounds, or other phosphonic polyvinylsulfonic acids, and combinations thereof; wherein the polymeric or elastomeric polymer comprises an adhesive polymer or wherein the electrode further comprises an adhesive polymer; and wherein the coalesced polymeric particles comprise a fluoropolymer.

GLOSSARY OF TERMS

The term "carbon nanotube" or "CNT" includes single, double and multiwall carbon nanotubes and, unless further specified, also includes bundles and other morphologies. The invention is not limited to specific types of CNTs. The CNTs can be any combination of these materials, for example, a CNT composition may include a mixture of single and multiwall CNTs, or it may consist essentially of DWNT and/or MWNT, or it may consist essentially of SWNT, etc. CNTs have an aspect ratio (length to diameter) of at least 50, preferably at least 100, and typically more than 1000. In some embodiments, a CNT network layer is continuous over a substrate; in some other embodiments, it is formed of rows of CNT networks separated by rows of polymer (such as CNTs deposited in a grooved polymer substrate). The CNTs may be made by methods known in the art such as arc discharge, CVD, laser ablation, or HiPco. The G/D ratio of CNTs is a well-known method for characterizing the quality of CNTs.

CNTs are attractive as electrodes because of their high charge storage capacity due to the high ratio between electrochemical surface area and geometric surface area (>600 m2/g) characteristic for the nanotube geometry, which gives rise to a large double-layer charge capacity.

The optical absorbance spectrum of CNTs is characterized by S22 and S11 transitions, whose positions depend upon the structure distribution of the CNTs and can be determined by a Kataura plot. These two absorption bands are associated with electron transitions between pairs of van Hove singularities in semiconducting CNTs.

Carbon nanotubes can be defined by purity factors that include percentage of metallic impurities (usually catalytic residues such as Fe, Mo, Co, Mn, etc,) and percentage of non-carbon nanotube impurities, which can be characterized by methods known in the art such as thermogravimetic analysis. The chemistry of the impurities can be determined by methods such as SEM-EDS, and x-ray diffraction (XRD). It is preferable to use carbon materials that have high purity, as these often have better combination of high conductivity and corrosion stability. Less than 1 to 2% metallic impurities are preferred. Carbons containing lower purity can also be substantially stabilized by this invention.

Glycosaminoglycans are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. Glycosaminoglycans are highly polar. Anionic glycosaminoglycans are characterized by having at some hydroxyl protons replaced by a counter ion; typically an alkali or alkaline earth element. Examples of glycosaminoglycans include: β-D-glucuronic acid, 2-O-sulfo-β-D-glucuronic acid, α-L-iduronic acid, 2-O-sulfo-α-L-iduronic acid, 3-D-galactose, 6-O-sulfo-β-D-galactose, β-D-N-acetylgalactosamine, β-D-N-acetylgalactosamine-4-O-sulfate, β-D-N-acetylgalactosamine-6-O-sulfate, β-D-N-acetylgalactosamine-4-O, 6-O-sulfate, α-D-N-acetylglucosamine, α-D-N-sulfoglucosamine, and α-D-N-sulfoglucosamine-6-O-sulfate. Hyaluronan is a particularly preferred glycosaminoglycan and representative of its class.

Sodium hyaluronate is the sodium salt of hyaluronic acid (HA). Hyaluron is a viscoelastic, anionic, nonsulfated glycosaminoglycan polymer (shown below). It is found naturally in connective, epithelial, and neural tissues. Its chemical structure and high molecular weight make it a good dispersing agent and film former. CNT/HA aqueous dispersion and phase diagram has been reported in the literature (Moulton et al. J. Am. Chem. Soc. 2007, 129(30), 9452). These dispersions may be used to create conductive films by casting the solution onto a substrate and allowing it to dry. However, the resulting films exhibit blistering, i.e. loss of adhesion, upon exposure to moisture or high humidity. In addition, they suffer from resistance fluctuations that occur as a result of moisture fluctuations, as HA can expand and contract, changing the junction resistance between CNT-CNT contacts.

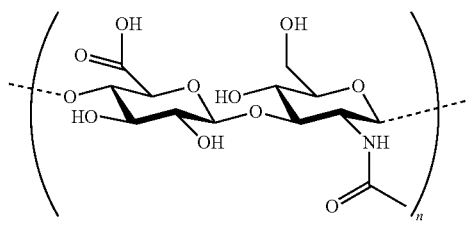

Materials such as sodium hyaluronate are natural products. These may be isolated from animal sources or extracted from bacteria.

The invention is often characterized by the term "comprising" which means "including," and does not exclude additional components. For example, the phrase "a dispersion comprising CNTs and an anionic glycosaminoglycan" does not exclude additional components and the dispersion may contain, for example, multiple types of glycosaminoglycan. In narrower aspects, the term "comprising" may be replaced by the more restrictive terms "consisting essentially of" or "consisting of." This is conventional patent terminology.

DETAILED DESCRIPTION OF THE INVENTION

The mixed-ionic-electronic conductors (MIECs) are an interconnected network of electrical and ionic conductors in an elastomeric matrix that provide: (1) high surface area for efficient capacitive charge-discharge; (2) high ionic conductivity for low interfacial resistance; (3) low ohmic resistance; and (4) excellent flexibility and toughness.

Electrical and ionic conductors are embedded in a matrix in such a way that the electrical and ionic elements achieve percolation, i.e., a continuous interconnected network, at lower loading than would be achieved by simple random mixing. This allows superior electrical performance to be achieved while retaining good mechanical properties.

Figure 1:
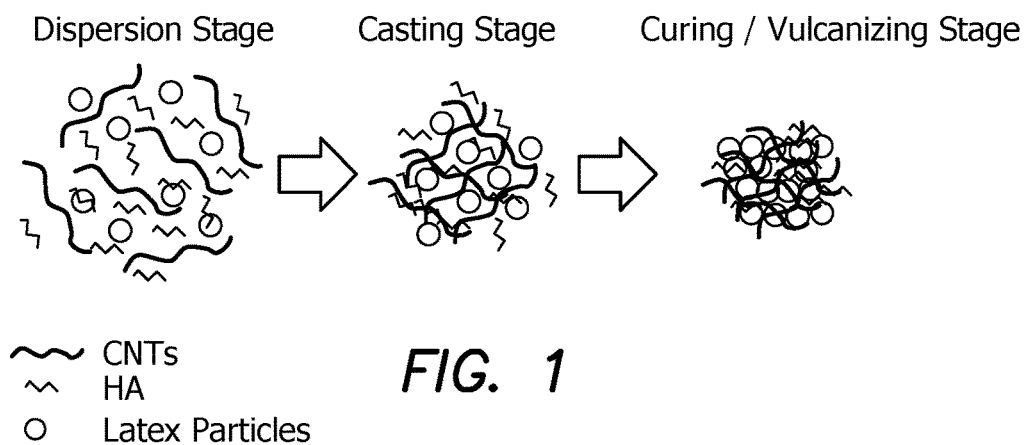
FIG. 1 is a schematic showing of the formation of MIEC.

The morphology may be controlled by using a polymer latex, in which polymer particles are dispersed in an aqueous phase, to template the organization of the electrical and ionic conductors, as shown in FIG. 1. Examples of suitable dispersions include elastomeric polymers such as nitrile butadiene rubber, natural rubber, silicone, Kraton-type, silicone acrylic, or polyurethane. Other suitable polymer lattices include polyvinylidene fluoride or polyvinylidene chloride. In such a dispersion, at least 90 mass % of the polymer particles are preferably in the range of 50 nm to 10 μm in diameter. The dispersion is cast and the volatiles (e.g., water) allowed to evaporate. During evaporation, the polymer particles coalesce to form a continuous fill. This process is the common one for creating nitrile gloves.

The electrical and ionic conductors are added to the latex so that they are dispersed in the aqueous phase. Methods known in the art for balancing the pH and selecting any necessary dispersing agents can be used. Suitable electrical conductors are those that have high aspect ratio and are readily dispersed into aqueous solutions and include carbon nanotubes, graphene and graphite structures, and metal nanowires. Suitable ionic conductors include sodium hyaluronate, also called hyaluronic acid, fluorosulfonic acids like Nafion™, sulfated polysaccharides and other mucoadhesive type compounds, or other phosphonic polyvinylsulfonic acids. Likewise, anisotropic ionic conductive particles like graphene oxide and modified graphene oxide may be used. In some embodiments, HA is preferred due to its tendency to hydrate with the skin, improving the skin contact.

By adding an electrical and ionic conductors to the dispersed phase of the latex, the conductors tend to coat the surface of the polymer particles, but not penetrate. As the latex is dried, the conductors tend to be confined at the interfaces, creating an interconnecting network, where the major phase is elastomeric and a connected thin, layer phase is the electronic/ionic conductors.

The morphology of this network can be modified by changing the particle size of the polymer in the latex. Larger particle sizes require less conductor to reach an interconnected phase. The film formation temperature is also a tunable parameter that can used to modify the kinetics to achieve various kinetically trapped states. Other methods to achieve better than random mixing include self-assembling or self-stratifying coatings.

In preferred embodiments, carbon nanotubes are the electrical conductors and hyaluronic acid (HA), or other glycosaminoglycan, along with moisture and ions, is the ionic conductor. Preferably, the MIECs have high conductivity of at least 1000 mS/cm, preferably at least 2000 mS/cm, or in the range of 2000 mS/cm to about 4000 mS/cm is desirable. In some preferred embodiments, the MIECs have high moisture retention such that the composite may absorb at least 20% water, up to 50% by mass water (corresponding to 100% of the weight of the dry composite), in some embodiments 20% to 50%, or 35% to 50% water.

In some embodiments, the ionic element is organized into a gradient structure, getting progressively richer as the material gets closer to the skin. The electrode performance is improved by introducing a smooth transition from electronic conduction interface (from the current collector/Electrode interface) to ionic conduction interface (from the skin-to-electrode-interface). A gradient can be prepared by layer-by-layer fabrication of the electrode, with increasing levels of ionic conductor in successive layers.

The invention could also involve combining two functionalities into one polymer, for example, an elastomer with ionic conductivity. This can be achieved, for example, with grafting of ionic segments from the polymer backbone. The ionic segments can be anionic, cationic or amphoteric. One method of grafting ionic segment is via co-polymerizing ion-containing monomers with non-ion-containing monomers. Another way of grafting ionic segment is via post functionalizing the elastomeric polymer.

Examples of anionic segments include, but not limited to, sulfonic, carboxylic, phosphonic and combinations thereof. Examples of cationic segments includes alkyl ammonium derivatives such as the N,N-dimethyl amino ethyl functionality. Examples of amphoteric segments includes the combination of anionic and cationic segments.

Examples of grafting anionic segments include, but are not limited to, co-polymerizing anion containing monomer such as styrene sulfonic acid with non-ion containing monomers such as styrene and butadiene to produce anion containing styrene-butadiene elastomer, namely sulfonated styrene-butadiene elastomer.

Examples of grafting cationic segments include, but are not limited to, co-polymerizing cation containing monomer such as N,N-dimethyl aminoethyl methacrylate with non-ion containing monomers such as styrene and butadiene to produce cation containing styrene-butadiene elastomer, namely aminated styrene-butadiene elastomer.

Examples of grafting amphoteric segments include, but are not limited to, co-polymerizing anion and cation containing monomer such as styrene sulfonic acid and N,N-dimethyl aminoethyl methacrylate with non-ion containing monomers such as styrene and butadiene to produce amphoteric ion containing styrene-butadiene elastomer, namely sulfonated and aminated styrene-butadiene elastomer.

Examples of post functionalizing the elastomeric polymer include, but are not limited to, treating styrene butadiene elastomer with fuming sulfuric acid to produce anion-containing styrene-butadiene elastomer, namely sulfonated styrene-butadiene elastomer.

Ion-containing monomers can be introduced into nitrile elastomers, polyurethane elastomers, silicone elastomers, poly aryl ether elastomers, polyphasphazene elastomers, acrylate elastomers, poly vinyl ether elastomers, perfluorinated polymeric elastomers, and the like.

The invention includes methods of making electrodes according to the descriptions provided herein.

The present invention is useful for making elastomers, preferably as cuffs or individually deposited electrodes. It is also useful for making electrodes with adhesive properties. The polymer matrix may include an adhesive-type polymer for skin adhesion.

Treatment Methods

Figure 6:
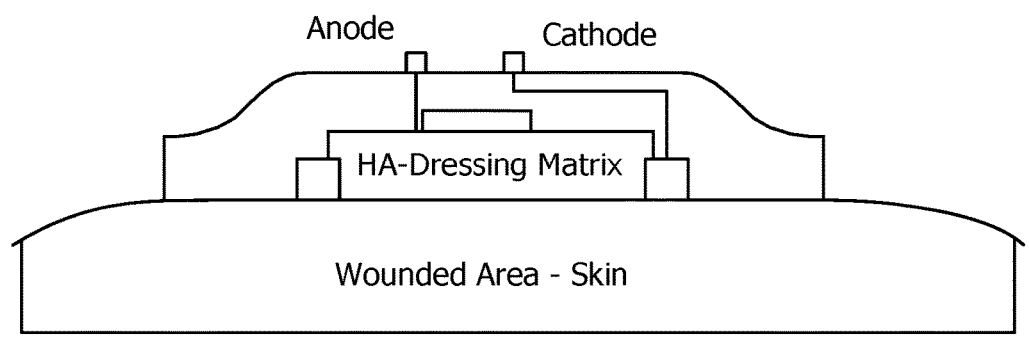
FIG. 6 schematically illustrates an apparatus for iontophoresis.

The inventive electrode composition can be used in neuromuscular electrical stimulation (NMES) and iontophoretic drug delivery. In iontophoresis, an HA dressing matrix is powered by an assembly as illustrated in FIG. 6.

Method of Making/Examples

CNTs are commercially available and a dispersion can be formed by mixing with an aqueous solution of HA, and optionally with ultrasound. The CNT/HA dispersion is combined with an elastomer dispersion. In the examples, the dispersion was a commercial nitrile-butadiene dispersion commonly used for manufacturing nitrile gloves. The resulting dispersions can be tape cast into a robust, flexible, freestanding composite film, which can then be peeled off and cut into desired size and shape for an electrode.

The process used to create these composites allows a very low loading of CNTs to be used and still reach saturation conductivities. The process starts with an elastomeric dispersion. For the examples in this disclosure, Zeon LX550L nitrile butadiene rubber was used. This material is a latex of acrylonitrile butadiene copolymer (NBR latex). In such a dispersion, the polymer particles are primarily 50 nm to 10 μm in diameter. The dispersion is cast and the volatiles (e.g. water) allowed to evaporate. During evaporation, the polymer particle coalesce to form a continuous film. This process is the common one for creating nitrile gloves.

By adding a CNT/HA dispersion to this latex, the CNT and HA tend to coat the surface of the polymer particles, but not penetrate into the particles. The CNT/HA dispersion is prepared by mixing purified CNTs (0.1 to 1 wt %) and HA (0.1 to 5 wt %) in water with the assistance of sonication. Hyaluronic acid sodium salt was from *Streptococcus Equi.* and carbon nanotubes are purified single wall carbon nanotubes obtained from OCSiAl (<1% metallic impurities).

As the latex is dried, the CNT/HA tends to be confined at the interfaces, creating an interconnecting network, where the major phase is elastomeric and a connected thin, layer phase is CNT/HA, or the electronic/ionic conductors.

The morphology of this network can be modified by changing the particle size of the polymer in the latex. Larger particle sizes require less CNT/HA to reach an interconnected phase. The film formation temperature is also a tunable parameter that can used to modify the kinetics to achieve various kinetically trapped states.

The final films are 85-90% polymer, 0.2 to 2 wt % CNT, and 0.2 to 4 wt % HA.

As a comparative example, CNTs were randomly mixed in a silicone elastomer using typical compounding methods. The resulting composite had a conductivity that was 20 times less than the corresponding sample made according to the method of this Example.

Figure 2:
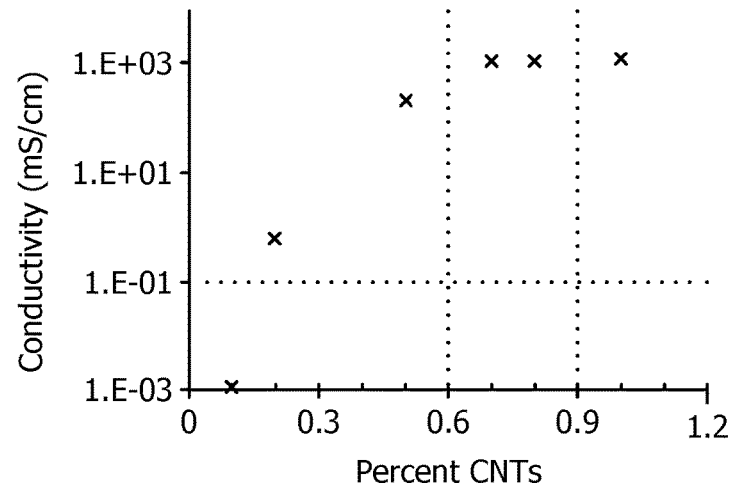
FIG. 2 shows bulk conductivity vs. CNT solid loading.

FIG. 2 shows the bulk conductivity of a flexible electrode as a function of the CNT loading. Bulk conductivity begins to increase near 0.2 wt % CNTs, associated with achieving a percolating network of CNTs. The percolating network allows a conductive pathway for electron carriers. As the loading of the CNTs increases, the conductivity of the electrode approaches a plateau. A conductivity of about 3000 mS/cm was obtained for an electrode composed of 1% CNTs and 1.2% HA in elastomer. The elastomer-CNT-HA electrode exhibits robustness to repeated stretching cycles. The film resistance shows negligible change after repeated stretching to 50% strain. The ionic conductivity and low interfacial resistance are provided by the HA and any moisture in the electrode.

As a comparative example, CNTs were randomly mixed in a silicone elastomer using typical compounding methods. The resulting composite had a conductivity that was 20 times less than the corresponding sample made according to the method of Example 1.

Figure 3:
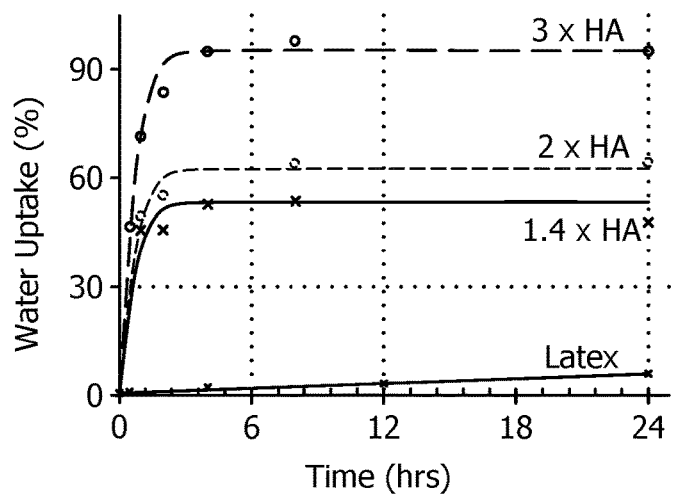
FIG. 3 shows water uptake at different HA mass ratios.

FIG. 3 shows the water uptake of flexible electrode as a function of time in water. The results indicate the affinity for water increases with increased HA content. The electrical resistance of the film was stable for a mass ratio of HA/CNT of about 2; above that value there was a loss of electrical conductivity, which may be due to expanded CNT-CNT junctions.

Figure 4:
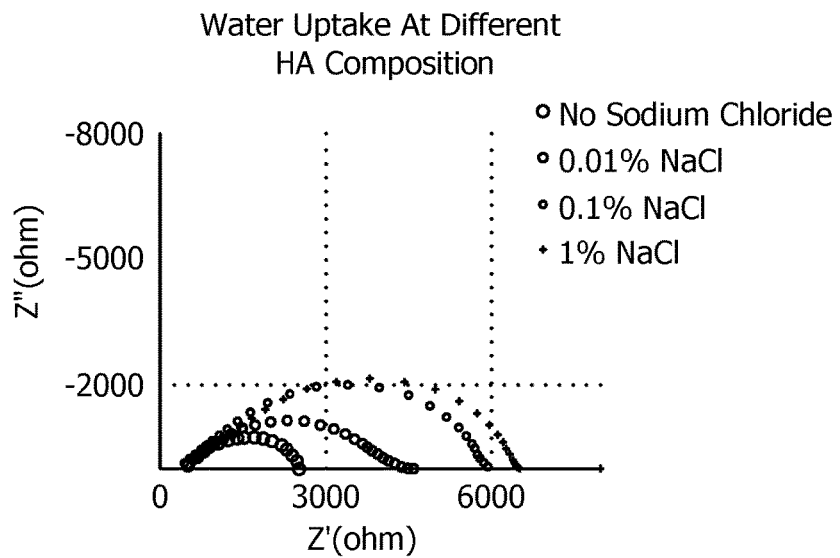
FIG. 4 shows water uptake at different HA sodium doping levels.

The electrochemical performance of the elastomer-CNT-HA flexible electrodes was characterized by electrochemical impedance spectroscopy (EIS). The samples were assembled into a fixture using two identical ionic block electrodes (working and reference). The impedance is measured in a frequency domain (from 1 MHz to 1 Hz) by applying a small electrical perturbation namely voltage (10 mV) and recording the real and imaginary parts of the complex resistance. The obtained Nyquist plots the frequency dependence of the complex resistance for an electrode made of 0.11 wt % CNTs and 0.15 wt % HA in elastomer with different ionic ($Na^+$) content are shown in FIG. 4. From the plots, it can be seen that the bulk resistance remains constant with increasing $Na^+$ loading. The Randles cell model embedded in FIG. 4 was used to fit the obtained EIS data. The Randles model includes a bulk resistance, a double layer capacitance and an ionic interfacial charge transfer. By introducing $Na^+$ into the elastomer-CNT-HA composite, the flexible electrode converts to a more ionic conductive material, resulting in an increase of ionic charge interfacial transfer resistance.

The total conductivity of the composite material is the sum of partial conductivity of charge carrier expressed as $$\sigma = F\Sigma c_i |z_i| u_i$$

Where F, c, z, and u are Faraday constant, concentration, charge number and mobility, respectively. The ratio of partial conductivity of a charge carrier to the total conductivity is defined as transference number of this charge carrier as $$t_i = \frac{\sigma_i}{\sigma_{tot}}$$

According to the electrochemical impedance spectroscopy (EIS) measurement shown in FIG. 4, one can calculate the ionic transference number as a function of doping amount (sodium ion) in composite material. As shown Table 1, the ionic transference number increased by increasing the doping level.

TABLE 1

| Doping level (as NaCl %) | $t_{Na+}$ |
|---|---|
| 0 | 0.07 |
| 0.01 | 0.13 |
| 0.1 | 0.17 |
| 1 | 0.19 |

The incorporation of 0.1 wt % to 1 wt % sodium made no significant difference on the ionic transference number. At 1 wt % NaCl, the ionic conductivity is approaching 20% of total conductivity which is higher than the pure metallic material.

Figure 5:
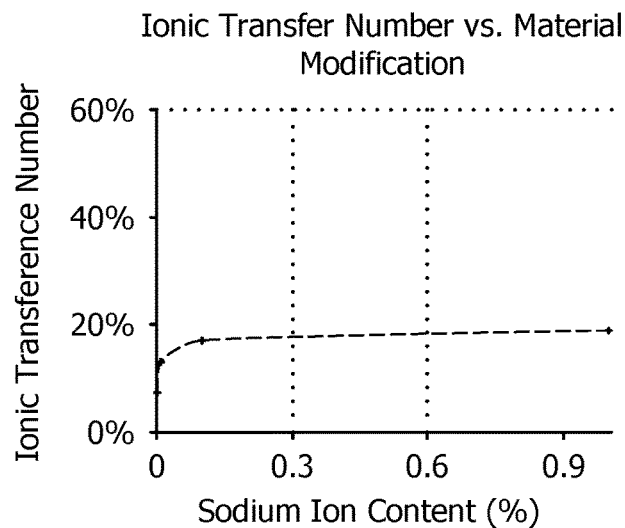
FIG. 5 is a plot of ionic transfer number vs. material modification.

As shown in FIG. 5, the extent of the ionic conductivity, ionic transference number, in overall electrical performance of the film can easily be tuned by simply varying the Na$^+$ content in HA component of the composite material. Increasing ionic transference number above 20% can be achieved by increasing the mass ratio of HA/CNT above about 3.

Tensile testing was carried out by creating tensile test samples and testing on Instron. These materials had constant loading of HA but increasing CNT. As shown in Table 2, the modulus and strength increased by the addition of CNTs. The addition of 0.2 wt % to 0.5 wt % made no difference on the elongation. At 1 wt % CNT, the elongation was slightly decreased but still high.

TABLE 2

|  | 0% CNTs | 0.2% CNTs | 0.5% CNTs | 1% CNTs |
|---|---|---|---|---|
| Modulus at 300% (MPa) | 0.401 | 0.697 | 1.052 | 1.528 |
| Modulus at 500% (MPa) | 0.406 | 0.704 | 1.029 | 1.520 |
| Tensile Stress at Max Load (MPa) | 0.654 | 0.821 | 1.164 | 1.722 |
| Maximum Extension | 1805 | 1806 | 1806 | 1491 |
| Stress at Max Extension | 0.633 | 0.814 | 1.019 | 1.269 |

Self-Adhesive Conductive Electrode

Figure 7:
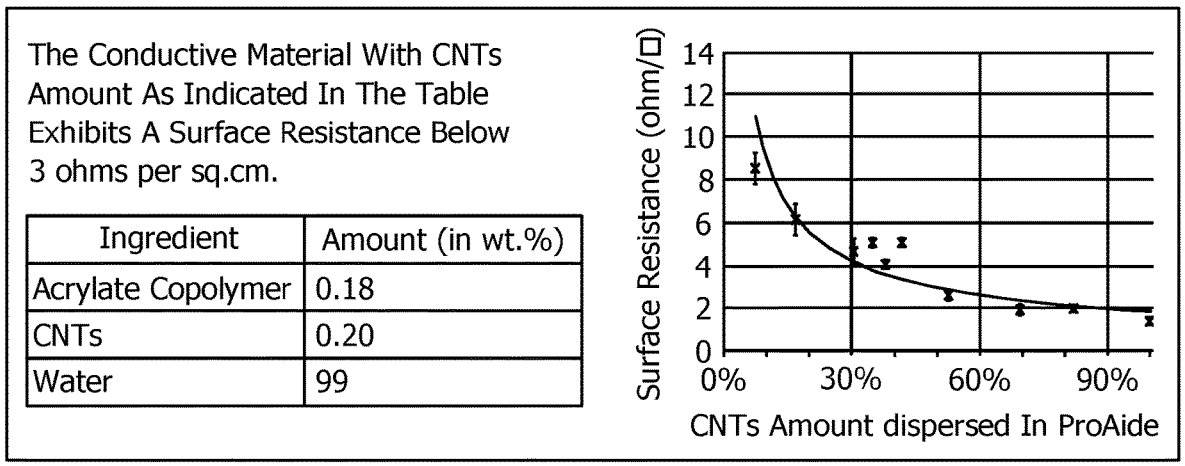
FIG. 7 illustrates surface resistance as a function of CNT loading for CNTs dispersed in an acrylate copolymer.

A self-adhesive acrylate copolymer water based emulsified is identified by trade name Pro-Aides, and Ghost Bond™. In a suitably sized vessel equipped with a suitable overhead mechanical stirrer (IKA overhead Model RW-20 manufactured by IKA-WERK, Germany), the water and acrylate copolymer emulsion are added at room temperature and mixed. Stirring is slowly increased until a vortex forms in the aqueous solution. The CNTs dispersed in HA aqueous solution, is slowly added to the vortex and allowed to mix until a uniform in composition is formed. The surface resistance obtained using 4-point measurement as a function of CNTs amount is shown in the FIG. 7.

Other polymeric matrix capable for producing high performance medical grade conductive electrode Polyurethane (PU)

Figure 8:
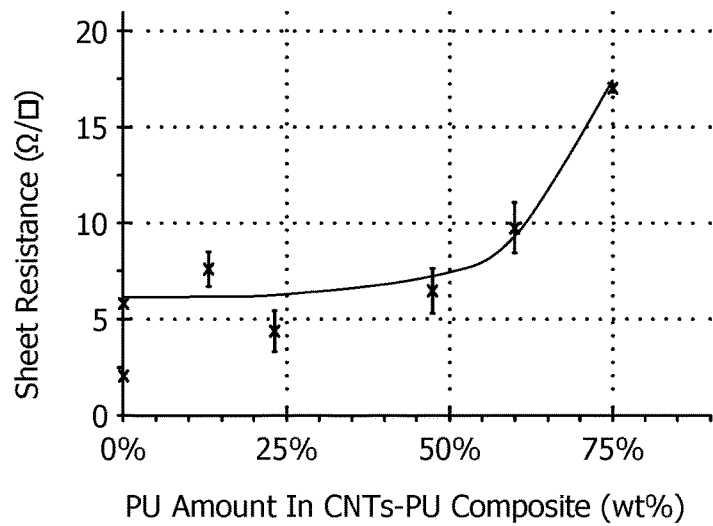
FIG. 8 illustrates sheet resistance as a function of CNT loading for a CNT-polyurethane composite.

A CNT aqueous dispersion prepared using ultrasonic treatment was mixed with as received Polyurethane emulsion in mass ratio indicated in the table below. A speed mixer such as FlackTek DAC 150 was used to homogenized CNTs into the polyurethane matrix. The surface resistance as a function of polymer content is shown in FIG. 8. From the figure it can be concluded that up to 50 wt % based on dry mass, the conductivity is similar to the conductivity of pure CNTs layer. In addition, the threshold amount of polyurethane at which the resistance increases drastically is about 50 wt %.

Fluoro-Polymers Such as PVDF and Teflon

Figure 9:
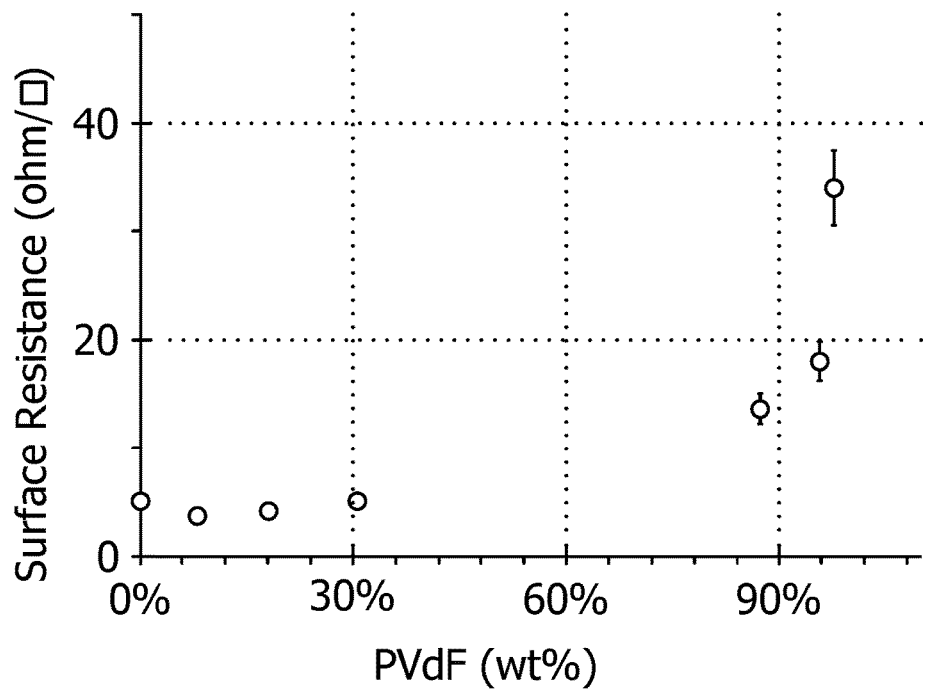
FIG. 9 illustrates surface resistance as a function of CNT loading for CNTs dispersed in PVDF.

A CNT aqueous dispersion prepared using ultrasonic treatment was mixed with an as-received fluoropolymer emulsion (such as PVDF) at different mass ratios. A speed mixer such as FlackTek DAC 150 was used to homogenized CNTs into a fluoropolymer matrix. The surface resistance as a function of PVDF is shown in the FIG. 9. Up to 30 wt % PVDF the conductivity of CNTs-PVDf composite material remains almost constant and a drastic increase of surface resistance occurs when the amount of PVDF in the matrix is higher than about 90 wt %.

Figure 10:
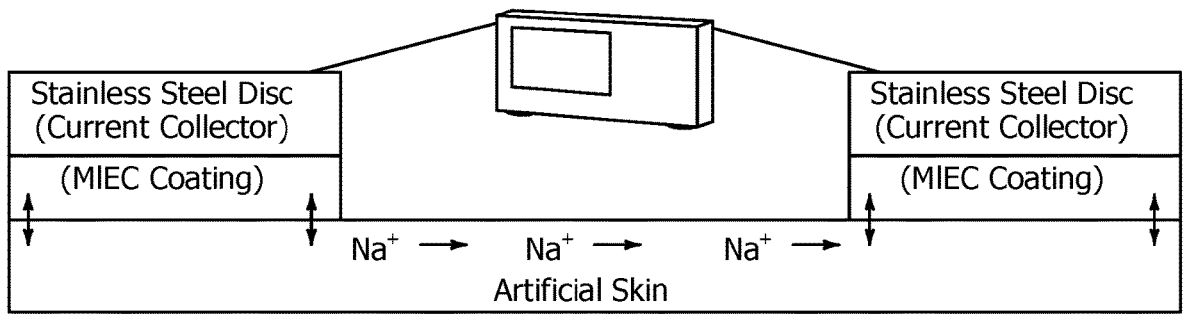
FIG. 10 illustrates the test set-up to for examining the performance with skin simulant.

The performance of different electrodes was tested with a skin simulant, using the set-up shown in FIG. 10. SynDaver synthetic human tissue model was used for evaluation of the electrodes. Stainless steel discs were used as a current collectors. The electrode of interest (MIEC coating) was applied to the stainless steel disk and then contacted with the synthetic skin. Impedance Spectroscopy testing was performed with two electrodes; impedance was measured in the frequency domain from 1 MHz to 1 Hz by applying a small perturbation voltage.

Figure 11:
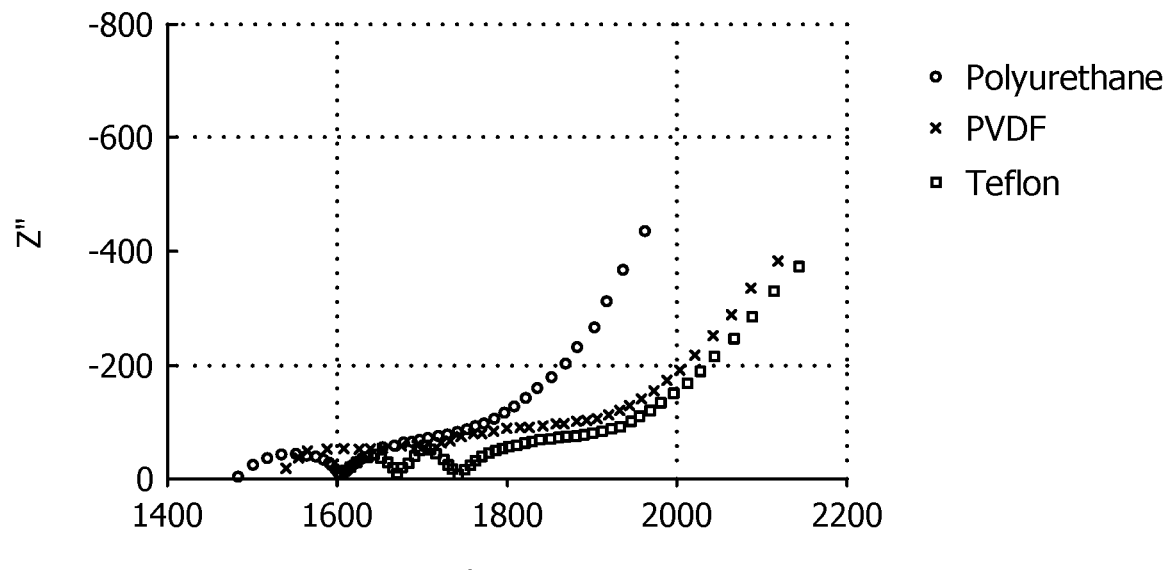
FIG. 11 illustrates impedance of CNT composites with three different polymeric materials.

The impedance of CNT electrodes prepared using different polymer materials such as Polyurethane (PU), PVDF and Teflon are shown in FIG. 11. As shown in the figure, by incorporation of polymeric material with different toughness and moisture affinity one can tailor the electrical performance and the interfacial charge transfer.

In preferred embodiments, the $t_i$ of the electrode is at least 0.10, preferably at least 0.13, in some embodiments in the range of 0.10 to about 0.20 or 0.15 to about 0.20. The electrode is doped with at least 0.01, or at least 0.10 or up to about 1 wt % sodium; or is doped with at least 0.01, or at least 0.10 or up to about 1 wt % sodium chloride.

Tensile testing was carried out by creating tensile test samples and testing on Instron. These materials had constant loading of HA but increasing CNT. As shown in Table 3, the modulus and strength increased with the addition of CNTs. The addition of 0.2 wt % to 0.5 wt % made no difference on the elongation. At 1 wt % CNT, the elongation was slightly decreased but still high.

TABLE 3

|  | 0% CNTs | 0.2% CNTs | 0.5% CNTs | 1% CNTs |
|---|---|---|---|---|
| Modulus at 300% (MPa) | 0.401 | 0.697 | 1.052 | 1.528 |
| Modulus at 500% (MPa) | 0.406 | 0.704 | 1.029 | 1.520 |
| Tensile Stress at Max Load (MPa) | 0.654 | 0.821 | 1.164 | 1.722 |
| Maximum Extension | 1805 | 1806 | 1806 | 1491 |
| Stress at Max Extension | 0.633 | 0.814 | 1.019 | 1.269 |

Some preferred embodiments of the invention can be further characterized by the above data; for example, a modulus at 300% of least 1 or 0.7 to about 1.5 MPa; or a tensile stress at maximum load of at least 0.8, or at least 1.1, or 0.8 to about 1.7 MPa; or a maximum extension of at least 1800 or about 1800; or a stress at maximum extension of at least 0.8 or at least 1.0, or 0.8 to about 1.3 MPa; or any combination of these characteristics (which may be further combined with any of the other characteristics described herein.

Electrode Gradient Design

In some embodiments, the ionic element is organized into a gradient structure, getting progressively richer as the material gets closer to the skin. The electrode performance is improved by introducing a smooth transition from electronic conduction interface (from the current collector/Electrode interface) to ionic conduction interface (from the skin-to-electrode-interface). A gradient can be prepared by layer-by-layer fabrication of the electrode, with increasing levels of ionic conductor in successive layers.

Figure 12:
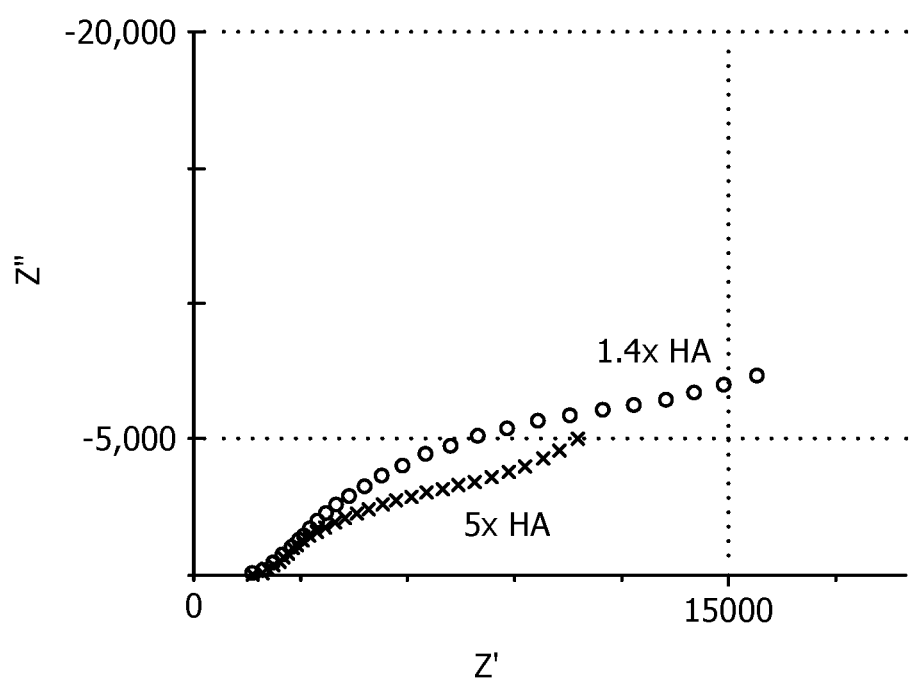
FIG. 12 shows impedance of MIEC with different amounts of HA.

The electrode performance is improved by introducing a smooth transition from electronic conduction interface (current collector/Electrode interface) to ionic conduction interface (skin-to-electrode-interface). FIG. 12 shows the Nyquist plot for two different MIEC compositions, with different ratios of HA/CNT. CNT loading was kept constant at 0.4 wt % of the electrode and the amount of HA was increased by decreasing the amount of solids from NBR. The interfacial resistance depends on HA loading. When it is too high, the interfacial and bulk conductivity decreases due to change in CNTs-CNTs connection. The use of a gradient allows better independent tuning of parameters.

The composition of an electrode with a gradient configuration is summarized in the following table 4.

TABLE 4

GRADIENT 1

|  | Component wt % | Ratio of HA/CNT |
|---|---|---|
| Layer Contacting Stainless Steel | | |
| CNT | 0.6 | 2.59 |
| HA | 1.6 | |
| Solids of Zeon NBR | 98 | |
| Layer in Middle | | |
| CNT | 0.85 | 3.70 |
| HA | 3.14 | |
| Solids of Zeon NBR | 96.01 | |
| Layer Contacting Skin | | |
| CNT | 0.27 | 3.76 |
| HA | 1.02 | |
| Solids of Zeon NBR | 98.71 | |

Figure 13:
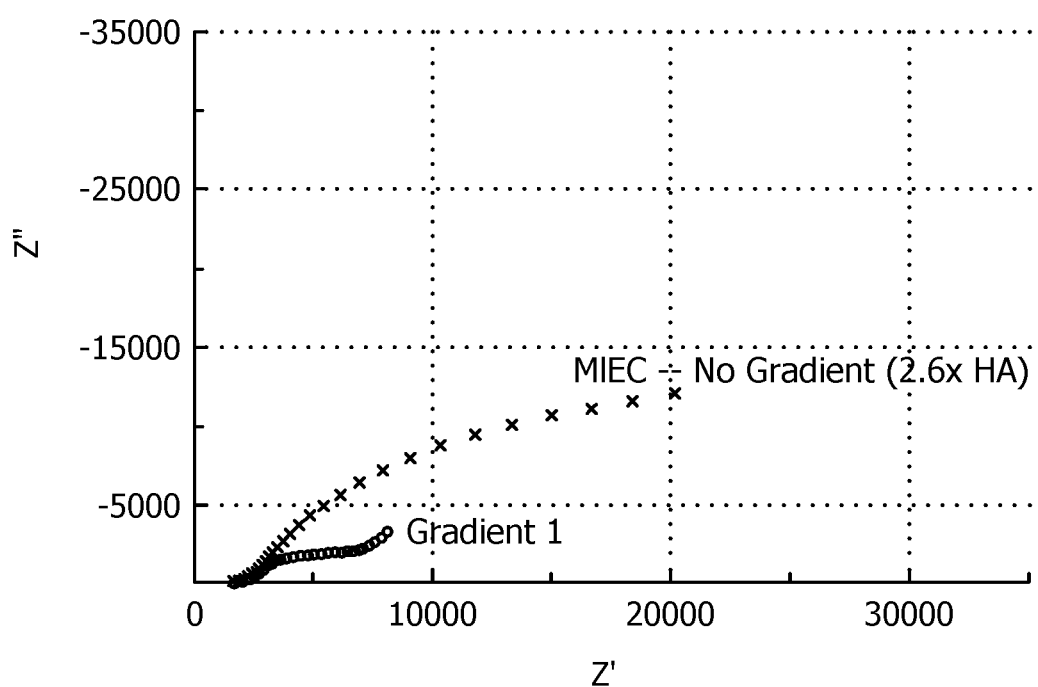
FIG. 13 shows impedance of a gradient electrode as compared with an ungraded electrode.

Its impedance, measured in a frequency domain (from 1 MHz to 1 Hz) with a small electrical perturbation namely voltage (10 mV), is compared with an electrode made of 0.4 wt % CNTs and 1.5 wt % HA in elastomer as shown in FIG. 13 ("non-gradient"). As shown in FIG. 13, the incorporation of gradient structure with 0.2 wt % to 0.8 wt % CNTs significantly improves the interfacial charge transfer as indicated by the small semi-circle in the Nyquist plot at medium and low frequency domain.

The data can be fit to a Randles cell model as discussed above, where the interfacial component of interest is described by a parallel circuit with capacitive (C2) and resistive (R2) elements. The gradient electrode is better described by two such parallel circuits but for comparison, the system was modeled as a resistor (R1) in series with one interfacial component. The results are shown in Table 5. As shown in Table 5, increasing the amount of HA to CNT in the non-gradient MIEC reduces the capacitance and increases the interfacial resistance. The gradient provides a system where these two can be decoupled, both C2 and R2 are lower for Gradient 1 than for MIEC 1.4X.

TABLE 5

| Sample: | xHA | CNTs (%) | R1 (Ohm): | C2 (nC): | R2 (Ohm): |
|---|---|---|---|---|---|
| MIEC 1.4X | 1.4 | 0.45 | 1655 | 3.427 | 192.5 |
| MIEC 2.6X | 2.6 | 0.44 | 1697 | 2.850 | 286.3 |
| MIEC 5.0X | 5.0 | 0.43 | 1671 | 2.482 | 219.1 |
| Gradient 1 | 2.59, 3.70, 3.76 | 0.62, 0.85, 0.27 | 1627 | 2.740 | 175.1 |
| Gradient 2 | 1.40, 2.58, 4.78 | 0.62, 0.86, 0.28 | 1791 | 2.904 | 198.6 |

Contemplated Example for Making Anionic Styrene Butadiene Elastomer:

In an emulsion reactor charge 51 mL of water, 3.5 grams of SDS and 0.2 grams of ascorbic acid. Maintain the temperature of the kettle around 4° C. Add 10 g of styrene 5 grams of SSA and 0.1 gram dodecyl mercaptan. Add of 10 mL of water containing 0.2 grams of potassium persulfate and 20 g of butadiene using a mass flow controller to the emulsion kettle at the same time for about 30 to One hour to produce sulfonated styrene butadiene elastomer product.

Ingredients
Range Wt (%)
Styrene 5-10
Butadiene 20-40
Styrene Sulfonic acid sodium salt (SSA) 1-5
Sodium dodecyl sulfate (SDS) 2-8
Dodecyl mercaptan 0.01-0.1
Potassium persulfate 0.01-0.2
Ascorbic acid 0.01-0.2
Water—Adjusted to 100 wt %

Contemplated Example for making cationic styrene butadiene elastomer: In an emulsion reactor charge 51 mL of water, 3.5 grams of CTAB and 0.2 grams of ascorbic acid. Maintain the temperature of the kettle around 4° C. Add 10 g of styrene 5 grams of NN-DMEMA and 0.1 gram dodecyl mercaptan. Add of 10 mL of water containing 0.2 grams of potassium persulfate and 20 g of butadiene using a mass flow controller to the emulsion kettle at the same time for about 30 to One hour to produce aminated styrene butadiene elastomer product.

Ingredients
Range Wt (%)
Styrene 5-10
Butadiene 20-40
N,N'-dimethyl aminoethyl methacrylate (NN-DMEMA) 1-5
Cetyl trimethyl ammonium bromide (CTAB) 2-8
Dodecyl mercaptan 0.01-0.1

Potassium persulfate 0.01-0.2
Ascorbic acid 0.01-0.2
Water—Adjusted to 100 wt %

What is claimed:

1. An electrode, comprising:
coalesced elastomer particles, carbon nanotubes (CNTs), and a glycosaminoglycan;
wherein the coalesced elastomer particles comprise exteriors;
wherein the CNTs and the glycosaminoglycan are dispersed in a matrix of the coalesced elastomer particles; and
wherein the CNTs and the glycosaminoglycan are disposed on the exteriors of the coalesced elastomer particles; wherein the electrode has a thickness and two major surfaces; and wherein at least 30 wt % of the CNTs are disposed on a major surface or within 10% of the thickness near the major surface.

2. The electrode of claim 1, comprising 0.4 to 4 wt % glycosaminoglycan.

3. The electrode of claim 1, comprising 10 to 60 wt % water.

4. The electrode of claim 1, comprising a mass ratio of the glycosaminoglycan to the CNT in a range of 0.5 to 5.

5. An apparatus for treating a patient comprising an array of the electrodes of claim 1.

6. An electrode, comprising:
coalesced polymeric particles, electrical conductor, and ionic conductor;
wherein the electrical conductor and the ionic conductor are dispersed in a matrix of the coalesced polymeric particles;
wherein the coalesced polymeric particles comprise exteriors;
wherein the electrical conductor and the ionic conductor are disposed on the exteriors of the coalesced polymeric particles; wherein the electrode comprises a top and bottom surface and the bottom surface is adapted to contact skin of a patient, wherein the electrode has a graded structure with an increasing ratio of the ionic conductor to the electrical conductor from the top to the bottom of the electrode.

7. The electrode of claim 6, wherein the polymeric particles are elastomeric; and wherein the electrode is made in a process wherein the electrical and ionic conductors are added to a dispersed phase of the coalesced polymeric particles.

8. The electrode of claim 6, wherein the graded structure is prepared by layer-by-layer fabrication of the electrode, with increasing levels of ionic conductor in successive layers; having at least 3 layers.

9. The electrode of claim 6, wherein the electrical conductor comprises particles having a height and a smallest width and wherein the particles have a number average aspect ratio of height to the smallest width dimension of at least 10.

10. The electrode of claim 6, wherein the electrical conductor comprises carbon nanotubes, graphene, graphite structures, and metal nanowires, and combinations thereof.

11. The electrode of claim 6, wherein the ionic conductor comprises hyaluronic acid, fluorosulfonic acids, sulfated polysaccharides and other mucoadhesive type compounds, or other phosphonic polyvinylsulfonic acids, and combinations thereof.

12. The electrode of claim 6, wherein the electrical conductor comprises carbon nanotubes (CNTs); wherein the electrode has a thickness and wherein at least 30 wt % of the CNTs are disposed on the bottom surface or within the 10% of the thickness near the bottom surface.

13. An electrode, comprising:
coalesced polymeric particles comprising ionically conductive moieties that are bonded to the coalesced polymeric particles, and electrical conductor;
wherein the coalesced polymeric particles comprise exteriors;
wherein the electrical conductor and ionically conductive moieties are disposed on the exteriors of the coalesced polymeric particles; wherein the electrode has a thickness and two major surfaces; and wherein at least 30 wt % of the CNTs are disposed on a major surface or within 10% of the thickness near the major surface.

14. The electrode of claim 13, wherein the ionically conductive moieties are covalently bonded to the coalesced polymeric particles.

15. The electrode of claim 13, wherein the coalesced polymeric particles comprise styrene-butadiene elastomer, nitrile elastomers, polyurethane elastomers, silicone elastomers, poly aryl ether elastomers, polyphasphazene elastomers, acrylate elastomers, poly vinyl ether elastomers, perfluorinated polymeric elastomers, and combinations thereof.

* * * * *